June 15, 1976 O. L. WEEKS Plant Pat. 3,909
CLIMBING ROSE PLANT
Filed June 24, 1975
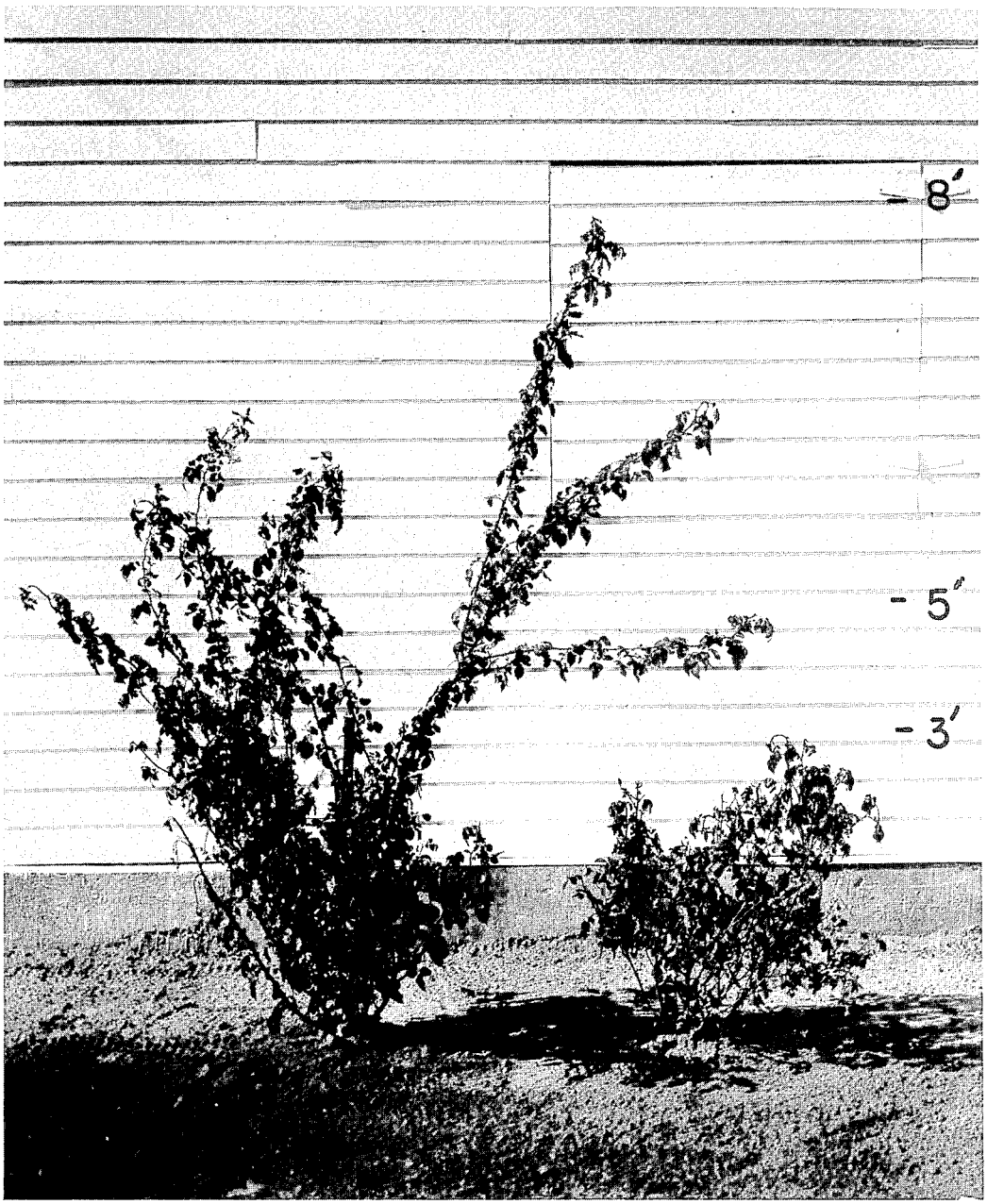

United States Patent

Plant Pat. 3,909

Patented June 15, 1976

3,909

CLIMBING ROSE PLANT

O. L. Weeks, 926 W. Philadelphia, Ontario, Calif. 91762

Filed June 24, 1975, Ser. No. 589,866

Int. Cl. A01h *5/00*

U.S. Cl. Plt.—4 1 Claim

The present invention relates to a new and distinct variety of rose plant of the climber class, which was discovered by me as a cultivated sport of the rose variety known as "Town Talk" (Plant Pat. No. 2,709), said discovery having been made in my rose growing fields located at Wasco, Calif.

At the time of my discovery, many plants of the parent variety "Town Talk" were being grown by me in my fields aforementioned. On one of my routine inspections of those plants, my attention was attracted to one particular plant which appeared to have produced a climbing cane, contrary to the bush habit of all of the other plants of "Town Talk." Upon closer inspection of this plant, I found that it had sported, so I took steps to preserve the sport and to asexually reproduce the same by budding, as performed by me in my regular growing fields at Wasco, aforesaid. Continued observations of the original sport and its progeny derived asexually therefrom by budding, conclusively confirmed its climbing habit and established that the new sport was substantially identical to the parent variety "Town Talk" except for the climbing habit aforesaid and for the fact that its flowers are produced on stems that grow as laterals from the climbing canes.

I have found that all of these distinguishing characteristics and distinctions of the new sport aforementioned are established and transmissible by asexual reproduction, and as far as I am aware, plants of the bush rose variety "Town Talk" have never previously exhibited a climbing habit of growth. I am therefore convinced that my new sport is definitely a new and distinct rose variety.

Being substantially identical to the parent variety in all respects except for the climbing habit which is evidenced by long and strong canes which attain an average mature height of 6 to 8 feet and which bear flowering stems which grow as laterals from the climbing canes, it is unnecessary to specifically describe the new sport in detail, since it otherwise substantially conforms to the detailed description embodied in Plant Pat. No. 2,709, issued Feb. 7, 1967, to which reference may be readily had.

For convenience, the accompanying drawing, in black-and-white, is presented to illustrate the climbing habit of growth of the new sport in comparison with the typical bush habit of a specimen plant of the parent variety "Town Talk."

I claim:

1. A new and distinct variety of rose plant of the climber class, substantially as herein shown and described, characterized particularly as to novelty by being substantially identical with its parent variety "Town Talk" (Plant Pat. No. 2,709), but essentially differing therefrom by its climbing habit of growth evidenced by the production of climbing canes which attain an average mature height of 6 to 8 feet, and by the habit of bearing its flowers on stems which grow as laterals from the climbing canes.

References Cited

UNITED STATES PATENTS

P.P. 2,709 2/1967 Swim et al. _____ 25

ROBERT E. BAGWILL, Primary Examiner

J. R. FEYRER, Assistant Examiner